(12) United States Patent
Audousset

(10) Patent No.: US 6,391,063 B1
(45) Date of Patent: *May 21, 2002

(54) COMPOSITION FOR THE OXIDATION DYEING OF KERATIN FIBERS AND DYEING PROCESS USING THIS COMPOSITION

(75) Inventor: Marie-Pascale Audousset, Asnieres (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/443,142

(22) Filed: Nov. 19, 1999

(30) Foreign Application Priority Data

Nov. 20, 1998 (FR) .............................. 98 14651

(51) Int. Cl.$^7$ ................................. A61K 7/13
(52) U.S. Cl. ..................... 8/407; 8/408; 8/409; 8/411; 8/416
(58) Field of Search ........................ 8/407, 408, 409, 8/411, 416

(56) References Cited

U.S. PATENT DOCUMENTS

| | | | |
|---|---|---|---|
| 3,061,432 A | 10/1962 | Menzel et al. | 430/376 |
| 3,227,554 A | 1/1966 | Barr et al. | 430/382 |
| 3,419,391 A | 12/1968 | Young | 430/387 |
| 3,725,067 A | 4/1973 | Bailey et al. | 430/476 |
| 3,926,631 A | 12/1975 | Arai et al. | 430/226 |
| 4,125,367 A * | 11/1978 | Bugaut et al. | 8/411 |
| 4,128,425 A | 12/1978 | Greenwald | 430/440 |
| 4,171,203 A * | 10/1979 | Rose et al. | 8/416 |
| 4,314,809 A * | 2/1982 | Rose et al. | 8/406 |
| 4,323,360 A * | 4/1982 | Bugaut et al. | 8/416 |
| 4,333,730 A * | 6/1982 | Bugaut et al. | 8/416 |
| 4,420,637 A * | 12/1983 | Bugaut et al. | 8/412 |
| 4,500,620 A | 2/1985 | Sato et al. | 430/386 |
| 4,854,935 A * | 8/1989 | Clausen et al. | 8/416 |
| 5,256,526 A | 10/1993 | Suzuki et al. | 430/384 |
| 5,376,146 A | 12/1994 | Casperson et al. | 8/408 |
| 5,441,863 A | 8/1995 | Tang et al. | 430/558 |
| 5,457,210 A | 10/1995 | Kim et al. | 548/262.4 |
| 5,645,610 A * | 7/1997 | Belzer et al. | 8/411 |
| 5,785,217 A | 7/1998 | Maubru et al. | 8/409 |
| 5,980,584 A * | 11/1999 | Lim et al. | 8/408 |
| 6,024,769 A * | 2/2000 | Cotteret | 8/411 |

FOREIGN PATENT DOCUMENTS

| | | |
|---|---|---|
| DE | 23 59 399 | 6/1975 |
| DE | 38 43 892 | 6/1990 |
| DE | 41 32 615 | 4/1993 |
| DE | 41 33 957 | 4/1993 |
| DE | 195 34 214 | 10/1996 |
| DE | 195 43 988 | 5/1997 |
| DE | 196 37 371 | 5/1998 |
| EP | 0 119 860 | 9/1984 |
| EP | 0 244 160 | 11/1987 |
| EP | 0 285 474 | 10/1988 |
| EP | 0 304 001 | 2/1989 |
| EP | 0 456 226 | 11/1991 |
| EP | 0 488 248 | 1/1992 |
| EP | 0 488 909 | 6/1992 |
| EP | 0 518 238 | 12/1992 |
| EP | 0 557 851 | 9/1993 |
| EP | 0 578 248 | 1/1994 |
| EP | 0 658 339 | 6/1995 |
| EP | 0 728 464 | 8/1996 |
| EP | 0 832 640 | 4/1998 |
| FR | 2 075 583 | 10/1971 |
| FR | 2 586 913 | 3/1987 |
| FR | 2 681 860 | 4/1993 |
| FR | 2 733 749 | 11/1996 |
| FR | 2 750 048 | 12/1997 |
| GB | 1 026 978 | 4/1966 |
| GB | 1 153 196 | 5/1969 |
| GB | 1 458 377 | 12/1976 |
| GB | 2 211 517 | 7/1989 |
| GB | 2 260 135 | 4/1993 |
| JP | 58-42045 | 3/1983 |
| JP | 59-99437 | 6/1984 |
| JP | 59-162548 | 9/1984 |
| JP | 59-171956 | 9/1984 |
| JP | 60-33552 | 2/1985 |
| JP | 60-43659 | 3/1985 |
| JP | 60-172982 | 9/1985 |
| JP | 62-279337 | 12/1987 |
| JP | 6-236011 | 8/1994 |
| JP | 7-36159 | 2/1995 |
| JP | 7-84348 | 3/1995 |
| JP | 7-92632 | 4/1995 |
| JP | 7-98489 | 4/1995 |
| JP | 7-244361 | 9/1995 |
| JP | 7-325375 | 12/1995 |
| WO | WO 94/08970 | 4/1994 |
| WO | WO 94/98969 | 4/1994 |
| WO | WO 96/15765 | 5/1996 |

OTHER PUBLICATIONS

Berichte der Deutschen Chemischen Gesellschaft, 1899, pp. 797–798, no month available.

Hans Beyer, Gerhard Wohler und Herbert Lemke: Über die Pyrazolbildung aus α–Chloracetessigester und und Thiocarbohydrazid, Chemische Berichte, vol. 89, No. 11, pp. 2550–2555, Aug. 1956.

(List continued on next page.)

Primary Examiner—Margaret Einsmann
(74) Attorney, Agent, or Firm—Finnegan Henderson Farabow Garrett & Dunner, L.L.P.

(57) ABSTRACT

The invention relates to a composition for the oxidation dyeing of keratin fibres, and in particular human keratin fibres such as the hair, comprising, in a medium which is suitable for dyeing, at least one oxidation base, 1,3-bis(β-hydroxyethyl)amino-2-methylbenzene and/or at least one of the addition salts thereof with an acid as first coupler, and at least one substituted meta-phenylenediamine as second coupler, as well as to the dyeing process using this composition.

31 Claims, No Drawings

OTHER PUBLICATIONS

Joseph Bailey, Synthesis of 1H–Pyrazolo–[3,20c]–s–Triazoles and Derived Azamethine Dyes, Journal of the Chemical Society, Perkin Transactions I, 18, 1977, pp. 2047–2052, no month available.

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyrimidines", Journal f. prakt. Chemie. Band 320, Heft 4, 1978, pp. 533–538, no month available.

Thomas Kauffmann et al., "Synthese von Amidrazonen aus Nitrilen und Natriumhydrazid", Chemische Berichte, vol. 97, No. 9, 1964, pp. 3436–3443, no month available.

E.J. Browne et al., "Triazoles. Part VII. Syntheses of Substituted 1,2,4–Triazoles", Journal of the Chemical Society, Dec. 1962, pp. 5149–5152.

Philip Magnus et al., "Synthesis of Helical Poly$\beta$–pyrroles. Multiple Atropisomerism Resulting in Helical Enantiomorphic Conformations", J. Am. Chem. Soc. vol. 112, No. 6, Mar. 14, 1990, pp. 2465–2468.

Von Dr. H. Gold, "Die Reaktion von Cyanurchlorid mit Dimethylformamid", Angew. Chem. vol. 72, No. 24, 1960, pp. 956–959, no month available.

Lidia Wyzgowska et al., "O Reakcjach Trikarboetoksymetanu. VIII", ACTA Poloniae Pharmaceutica, vol. 38, No. 307, 1981, pp. 83–88, no month available.

E. Hannig et al., "Zur Kenntnis des 4–aminierten Phenylbutazons", Die Pharamazie, 1980, pp. 231–236, no month available.

Mohamed Helmi Elnagdi et al., "Studies on 3,5–pyrazolidinediones. IV. Addition of 4–Arylazo–3,5–pyrazolidinediones to Ethyl Acrylate", Bulletin of the Chemical Society of Japan, vol. 46, No. 6, 1973, pp. 1830–1833, no month available.

Giuliana Cardillo et al., "Sulle 1,2–difenil–3,5–dichetopirazolidine—Prodotti di reazione con biossido di azoto", Gazzette Italiana, vol. 96, 1966, pp. 973–985, no month available.

Victor Israel Cohen, "A New Method of Synthesis of Some 2–Aryl and 2–Heterocyclic Benzimidazole, Benzoxazole and Benzothiazole Derivatives", Journal of Heterocyclic Chemistry, vol. 16, No. 1, Jan. 1979, pp. 13–16.

Mohamed I. Ali et al., "Reactions with Thiazolo[3,2–b]–s–triazol–3(2H)–ones", Journal f. prakt. Chemie, Bank 318, Heft 1, 1976, pp. 12–18, no month available.

S. Syed Shafi et al., "Studies on Biologically Active Heterocycles Part I. Synthesis and Antibacterial Activity of Some 2,5–Disubstituted–1,3,4–Oxadiazole, 1,3,4–Thiadiazole, 1,2,4–Triazole, and 4–Thiazolidinone", Indian Journal of Heterocyclic Chemistry, vol. 5, Oct.–Dec. 1995, pp. 135–138.

Eser Ilhan et al., "Synthese von 6–Benzyliden–2–($\alpha$, $\alpha$–diphenyl–$\alpha$–hydroxyacetyl)–thiazolo[3,2–b] s–triazol–5–onen als potentiell biologish wirksame Stoffe", Archiv der Pharmazie, vol. 327, No. 12, Dec. 1994, pp. 825–826.

Ferenc Korodi et al., "Fused 1,4,5–Triazole Heterocycles. III. Syntheses and Structures of Novel [1,2,4]triazolo[1,3] thiazinoquinolinest", Heterocyclic Communications, vol. 1, No. 4, 1995, pp. 297–306, no month available.

Dorothy Nickerson, "Color Tolerance Specification", Journal of the Optical Society of American, vol. 34, No. 9, Sep. 1944, pp. 550–570.

English language Derwent Abstract of DE 23 59 399, Jun. 1975.

English language Derwent Abstract of DE 38 43 892, Jun. 1990.

English language Derwent Abstract of DE 41 32 615, Apr. 1993.

English language Derwent Abstract of DE 41 33 957, Apr. 1993.

English language Derwent Abstract of DE 195 34, 214, Oct. 1996.

English language Derwent Abstract of DE 195 43 988, May 1997.

English language Derwent Abstract of DE 196 37 371, Mar. 1998.

English language Derwent Abstract of EP 0 488 909, Jun. 1992.

English language Derwent Abstract of EP 0 728 464, Aug. 1996.

English language Derwent Abstract of EP 0 832 640, Apr. 1998.

English language Derwent Abstract of FR 2 075 583, Oct. 1971.

English language Derwent Abstract of FR 2 586 913, Mar. 1987.

English language Derwent Abstract of FR 2 681 860, Apr. 1993.

English language Derwent Abstract of FR 2 733 749, Nov. 1996.

English language Derwent Abstract of FR 2 750 048, Dec. 1997.

English language Derwent Abstract of JP 58–42045, Mar. 1983.

English language Derwent Abstract of JP 59–99437, Jun. 1984.

English language Derwent Abstract of JP 59–162548, Sep. 1984.

English language Derwent Abstract of JP 59–171956, Sep. 1984.

English language Derwent Abstract of JP 60–33552, Feb. 1985.

English language Derwent Abstract of JP 60–43659, Mar. 1985.

Henryk Foks et al., "Synthesis and Biological Activity of Thiazolo–1,2,4–Triazoles", Acta Poloniae Pharmaceutica, vol. 52, No. 5, Sep./Oct. 1995, pp. 415–520.

English language Derwent Abstract of JP 60–172982, Sep. 1985.

English language Derwent Abstract of JP 62–279337, Dec. 1987.

English language Derwent Abstract of JP 6–236011, Aug. 1994.

English language Derwent Abstract of JP 7–36159, Feb. 1995.

English language Derwent Abstract of JP 7–84348, Mar. 1995.

English language Derwent Abstract of JP 7–92632, Apr. 1995.

English language Derwent Abstract of JP 7–98489, Apr. 1995.

English language Derwent Abstract of JP 7–244361, Sep. 1995.

* cited by examiner

COMPOSITION FOR THE OXIDATION DYEING OF KERATIN FIBERS AND DYEING PROCESS USING THIS COMPOSITION

The invention relates to a composition for the oxidation dyeing of keratin fibres, and in particular human keratin fibres such as the hair, comprising, in a medium which is suitable for dyeing, at least one oxidation base, 1,3-bis(β-hydroxyethyl)amino-2-methylbenzene and/or at least one of the addition salts thereof with an acid as first coupler, and at least one substituted meta-phenylenediamine as second coupler, as well as to the dyeing process using this composition.

It is known practice to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes must moreover satisfy a certain number of requirements. Thus, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible coloration differences along the same length of keratin fibre, which may in fact be differently sensitized (i.e. damaged) between its tip and its root.

Compositions for the oxidation dyeing of keratin fibres containing one or more oxidation bases, one or more 2,6-diaminotoluene derivatives as coupler, and optionally one or more additional couplers chosen from the couplers conventionally used in the field of oxidation dyeing, have already been proposed, in particular in patent applications FR-A-2,681,860 and DE-A-19,637,371. However, although the colorations obtained using such compositions are highly chromatic, they are not entirely satisfactory, in particular as regards their fastness with respect to the various treatments and natural attacking factors to which keratin fibres may be subjected.

The Applicant has now discovered that it is possible to obtain novel dyes which are capable of giving intense and highly chromatic colorations, and which show good resistance to the various attacking factors to which the fibres may be subjected, by combining at least one oxidation base, 1,3-bis(β-hydroxyethyl)amino-2-methylbenzene and/or at least one of the addition salts thereof with an acid as first coupler, and at least one suitably selected substituted meta-phenylenediamine as second coupler.

This discovery forms the basis of the present invention.

A first subject of the invention is thus a composition for the oxidation dyeing of keratin fibres, and in particular human keratin fibres such as the hair, characterized in that it comprises, in a medium which is suitable for dyeing:
  at least one oxidation base,
  1,3-bis(β-hydroxyethyl)amino-2-methylbenzene and/or at least one of the addition salts thereof with an acid, as first coupler;
  and at least a second coupler chosen from the substituted meta-phenylenediamines of formula (I) below, and the addition salts thereof with an acid:

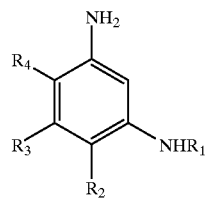

(I)

in which:
  $R_1$ represents a hydrogen atom, a $C_1$–$C_4$ alkyl radical, a $C_1$–$C_4$ monohydroxyalkyl radical or a $C_2$–$C_4$ polyhydroxyalkyl radical;
  $R_2$ and $R_3$, which may be identical or different, represent a hydrogen atom, a $C_1$–$C_4$ alkyl radical or a $C_1$–$C_4$ hydroxyalkoxy radical;
  $R_4$ represents a $C_1$–$C_4$ alkoxy radical, a $C_1$–$C_4$ aminoalkoxy radical, a $C_1$–$C_4$ monohydroxyalkoxy radical, a $C_2$–$C_4$ polyhydroxyalkoxy radical or a 2,4-diaminophenoxyalkoxy radical;
it being understood that when $R_1$, $R_2$ and $R_3$ simultaneously represent a hydrogen atom, then $R_4$ is other than a methoxy radical.

The dye composition in accordance with the invention gives intense, highly chromatic colorations which have excellent properties of resistance with respect both to atmospheric agents such as light and bad weather and to perspiration and the various treatments to which the hair may be subjected. These properties are particularly noteworthy especially as regards the resistance of the colorations towards the action of permanent-waving.

A subject of the invention is also a process for the oxidation dyeing keratin fibres using this dye composition.

Among the substituted meta-phenylenediamines of formula (I) above which may be mentioned more particularly are 2,4-diaminophenoxyethanol, 2,4-diamino-1-ethoxybenzene, 2-amino-4-N-(β-hydroxyethyl)aminoanisole, 3,5-diamino-1-ethyl-2-methoxybenzene, 3,5-diamino-2-methoxy-1-methylbenzene, 1,3-bis(2,4-diaminophenoxy)propane, bis-(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxy-propyloxy)benzene and 2-amino-4-N-(β-hydroxyethyl)-amino-1-methoxybenzene and the addition salts thereof with an acid.

The nature of the oxidation base(s) used in the ready-to-use dye composition is not critical. They can be chosen in particular from para-phenylenediamines, double bases, para-aminophenols, ortho-aminophenols and heterocyclic oxidation bases.

Among the para-phenylenediamines which can be used as oxidation base in the dye compositions in accordance with the invention, mention may be made in particular of the compounds of formula (II) below, and the addition salts thereof with an acid:

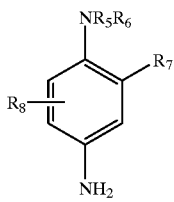

(II)

in which:
- $R_5$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous, phenyl or 4'-aminophenyl group;
- $R_6$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous group;
- $R_7$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, a $C_1$–$C_4$ acetylaminoalkoxy radical, a $C_1$–$C_4$ mesylaminoalkoxy radical or a $C_1$–$C_4$ carbamoylaminoalkoxy radical,
- $R_8$ represents a hydrogen or halogen atom or a $C_1$–$C_4$ alkyl radical.

Among the nitrogenous groups of formula (II) above which may be mentioned in particular are amino, mono($C_1$–$C_4$)alkylamino, di($C_1$–$C_4$)alkylamino, tri($C_1$–$C_4$) alkylamino, monohydroxy($C_1$–$C_4$)alkylamino, imidazolinium and ammonium radicals.

Among the para-phenylenediamines of formula (II) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylene-diamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine,N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines of formula (II) above which are most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

According to the invention, the expression "double bases" means compounds comprising at least two aromatic nuclei bearing amino and/or hydroxyl groups.

Among the double bases which can be used as oxidation bases in the dye compositions in accordance with the invention, mention may be made in particular of the compounds corresponding to formula (III) below, and the addition salts thereof with an acid:

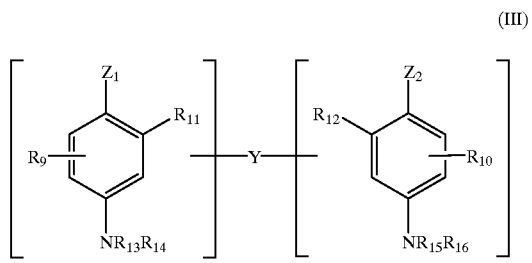

(III)

in which:
- $Z_1$ and $Z_2$, which may be identical or different, represent a hydroxyl or —$NH_2$ radical which can be substituted with a $C_1$–$C_4$ alkyl radical or with a linker arm Y;
- the linker arm Y represents a linear or branched alkylene chain comprising from 1 to 14 carbon atoms, which can be interrupted or terminated with one or more nitrogenous groups and/or with one or more hetero atoms such as oxygen, sulphur or nitrogen atoms, and optionally substituted with one or more hydroxyl or $C_1$–$C_6$ alkoxy radicals;
- $R_9$ and $R_{10}$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
- $R_{11}$, $R_{12}$, $R_{13}$, $R_{14}$, $R_{15}$ and $R_{16}$, which may be identical or different, represent a hydrogen atom, a linker arm Y or a $C_1$–$C_4$ alkyl radical; it being understood that the compounds of formula (III) comprise only one linker arm Y per molecule.

Among the nitrogenous groups of formula (III) above which may be mentioned in particular are amino, mono($C_1$–$C_4$)alkylamino, di($C_1$–$C_4$)alkylamino, tri($C_1$–$C_4$) alkylamino, monohydroxy($C_1$–$C_4$)alkylamino, imidazolinium and ammonium radicals.

Among the double bases of formula (III) above which may be mentioned more particularly are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetra-methylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (III), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the para-aminophenols which can be used as oxidation bases in the dye compositions in accordance with the invention, mention may be made in particular of the compounds of formula (IV) below, and the addition salts thereof with an acid:

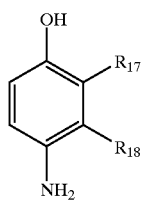

(IV)

in which:
- $R_{17}$ represents a hydrogen or halogen atom, a $C_1$–$C_4$ alkyl radical, a $C_1$–$C_4$ monohydroxyalkyl radical, a $(C_1$–$C_4)$ alkoxy$(C_1$–$C_4)$alkyl radical, a $C_1$–$C_4$ aminoalkyl radical or a hydroxy$(C_1$–$C_4)$alkylamino$(C_1$–$C_4)$alkyl radical,
- $R_{18}$ represents a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical, a cyano$(C_1$–$C_4)$alkyl radical or a $(C_1$–$C_4)$alkoxy $(C_1$–$C_4)$alkyl radical, it being understood that at least one of the radicals $R_{17}$ and $R_{18}$ represents a hydrogen atom.

Among the para-aminophenols of formula (IV) above which may be mentioned more particularly are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives which may be mentioned more particularly are the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, as well as pyrazolopyrimidine derivatives such as those mentioned in patent application FR-A-2,750,048 and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a] pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a] pyrimidine-3,7-diamine and 2,5-N-7, N-7-tetramethylpyrazolo[1,5-a]pyrimidine-3,7-diamine, and the addition salts thereof and the tautomers thereof, when a tautomeric equilibrium exists, and the addition salts thereof with an acid.

Among the pyrazole derivatives, mention may be made more particularly of the compounds described in patents or patent applications DE 3,843,892, DE 4,133,957, WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof with an acid.

The oxidation base(s) preferably represent(s) from 0.0005 to 12% by weight approximately relative to the total weight of the dye composition in accordance with the invention, and even more preferably from 0.005 to 6% by weight approximately relative to this weight.

The 1,3-bis(β-hydroxyethyl)amino-2-methylbenzene and/or the addition salt(s) thereof with an acid, which are used as first coupler according to the invention, preferably represent(s) from 0.001 to 10% by weight approximately relative to the total weight of the dye composition and even more preferably from 0.01 to 5% by weight approximately relative to this weight.

The substituted meta-phenylenediamine(s) of formula (I) in accordance with the invention preferably represent from 0.0001 to 10% by weight approximately relative to the total weight of the dye composition and even more preferably from 0.005 to 5% by weight approximately relative to this weight.

The dye composition in accordance with the invention can also contain one or more additional couplers other than 1,3-bis(β-hydroxyethyl)amino-2-methylbenzene and substituted meta-phenylenediamines of formula (I) and/or one or more direct dyes, in particular to modify the shades or to enrich them with glints.

Among the couplers which may additionally be present in the dye composition in accordance with the invention, mention may be made in particular of meta-aminophenols, meta-diphenols and heterocyclic couplers, and the addition salts thereof with an acid.

When they are present, these additional couplers preferably represent from 0.0001 to 10% by weight approximately relative to the total weight of the dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the dye composition in accordance with the invention generally consists of water or a mixture of water and at least one organic solvent to dissolve the compounds which would not be sufficiently soluble in water. Organic solvents which may be mentioned, for example, are $C_1-C_4$ alkanols, such as ethanol and isopropanol.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 12 approximately. It can be adjusted to the desired value using acidifying or basifying agents usually used for dyeing keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such as mono-, di- and triethanolamine, 2-methyl-2-aminopropanol and derivatives thereof, sodium hydroxide, potassium hydroxide and the compounds of formula (V) below:

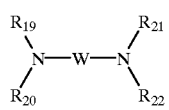

(V)

in which W is a propylene residue optionally substituted with a hydroxyl group or a $C_1-C_4$ alkyl radical; $R_{19}$, $R_{20}$, $R_{21}$ and $R_{22}$, which may be identical or different, represent a hydrogen atom or a $C_1-C_4$ alkyl or $C_1-C_4$ hydroxyalkyl radical.

The dye composition in accordance with the invention can also contain various adjuvants conventionally used in compositions for dyeing the hair.

Needless to say, a person skilled in the art will take care to select this or these optional additional compounds such that the advantageous properties intrinsically associated with the dye composition in accordance with the invention are not, or are not substantially, adversely affected by the addition(s) envisaged.

The dye composition in accordance with the invention can be in various forms, such as in the form of liquids, creams or gels, which are optionally pressurized, or in any other form which is suitable for dyeing keratin fibres, and in particular human hair.

A subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent which is added to the dye composition just at the time of use, or which is present in an oxidizing composition that is applied simultaneously or sequentially in a separate manner.

According to one particularly preferred embodiment of the dyeing process according to the invention, the dye composition described above is mixed, at the time of use, with an oxidizing composition comprising, in a medium which is suitable for dyeing, at least one oxidizing agent which is present in an amount which is sufficient to develop a coloration. The mixture obtained is then applied to the keratin fibres and is left to stand for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates, persalts such as perborates and persulphates, peracids, enzymes such as 2-electron oxidoreductases, peroxidases and lactases. Hydrogen peroxide is particularly preferred.

The pH of the oxidizing composition containing the oxidizing agent as defined above is such that, after mixing with the dye composition, the pH of the resulting composition applied to the keratin fibres preferably ranges between 3 and 12 approximately and even more preferably between 5 and 11. It is adjusted to the desired value using acidifying or basifying agents usually used for dyeing keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels, or in any other form which is suitable for dyeing keratin fibres, and in particular human hair.

Another subject of the invention is a multi-compartment dyeing device or multi-compartment dyeing "kit" or any other multi-compartment packaging system, a first compartment of which contains the dye composition as defined above and a second compartment of which contains the oxidizing composition as defined above. These devices can be equipped with a means for applying the desired mixture to the hair, such as the devices described in patent FR-2,586,913 in the name of the Applicant.

The examples which follow are intended to illustrate the invention without thereby limiting its scope.

EXAMPLES

Examples 1 to 3 of Dyeing in Alkaline Medium

The dye compositions below were prepared (contents in grams):

| EXAMPLE | 1 | 2 | 3 |
|---|---|---|---|
| para-Phenylenediamine (oxidation base) | 0.22 | — | — |
| N,N-Bis(β-hydroxyethyl)-para-phenylenediamine sulphate (oxidation base) | — | 0.63 | — |
| para-Aminophenol (oxidation base) | — | — | 0.22 |
| 1,3-Bis(β-hydroxyethyl)amino-2-methylbenzene (first coupler) | 0.21 | 0.21 | 0.21 |

-continued

| EXAMPLE | 1 | 2 | 3 |
|---|---|---|---|
| 2,4-Diaminophenoxyethanol dihydrochloride (coupler of formula (I)) | 0.24 | — | 0.24 |
| 2-Amino-4-N-(β-hydroxyethyl)-aminoanisole dihydrochloride (coupler of formula (I)) | — | 0.25 | — |
| Common dye support No. 1 | (*) | (*) | (*) |
| Demineralized water qs | 100 g | 100 g | 100 g |

| (*): Common dye support No. 1: | |
|---|---|
| 96° ethanol | 18 g |
| Sodium metabisulphite as an aqueous 35% solution | 0.68 g |
| Pentasodium salt of diethylenetriamine pentaacetic acid | 1.1 g |
| Aqueous ammonia containing 20% $NH_3$ | 10 g |

At the time of use, each of the dye compositions described above was mixed with an equivalent amount by weight of 20-volumes hydrogen peroxide (6% by weight) having a pH of about 3.

Each resulting mixture had a pH of about 10±0.2 and was applied for 30 minutes to locks of permanent-waved grey hair containing 90% white hairs.

The hair was then rinsed with water, washed with a standard shampoo, rinsed again and then dried.

The hair was dyed in the shades given in the table below:

| EXAMPLE | SHADE OBTAINED |
|---|---|
| 1 | Very intense ash-violet |
| 2 | Deep blue |
| 3 | Intense iridescent red |

Example 4 of Dyeing in Acidic Medium

The dye composition below in accordance with the invention was prepared:

| para-Phenylenediamine (oxidation base) | 0.22 g |
|---|---|
| 1,3-Bis(β-Hydroxyethyl)amino-2-methyl benzene (first coupler) | 0.21 g |
| 2,4-Diaminophenoxyethanol dihydro-chloride (coupler of formula (I)) | 0.24 g |
| 96° ethanol | 18 g |
| Sodium metabisulphite as an aqueous 35% solution | 0.68 g |
| Pentasodium salt of diethylenetriamine-pentaacetic acid | 1.1 g |
| $K_2HPO_4/KH_2PO_4$ (1.5M/1M) buffer | 10 g |
| Demineralized water qs | 100 g |

At the time of use, the dye composition described above was mixed with an equivalent amount by weight of 20-volumes hydrogen peroxide (6% by weight) having a pH of about 3.

The resulting mixture had a pH of about 6.8±0.2, and was applied for 30 minutes to locks of permanent-waved grey hair containing 90% white hairs.

The hair was then rinsed with water, washed with a standard shampoo, rinsed again and then dried.

The hair was dyed in a deep ash-violet shade.

Comparative Examples 5 and 6

The dye compositions below were prepared (contents in grams):

| EXAMPLE | 5 | 6(**) |
|---|---|---|
| para-Phenylenediamine (oxidation base) | 0.324 | 0.324 |
| 1,3-Bis(β-Hydroxyethyl)amino-2-methylbenzene (first coupler) | 0.315 | 0.315 |
| 2,4-Diaminophenoxyethanol dihydro-chloride (coupler of formula (I): $1.5 \times 10^{-3}$ mol) | 0.3615 | — |
| 2,4-Diamino-1-methoxybenzene dihydrochloride (coupler not forming part of the invention: $1.5 \times 10^{-3}$ mol) | — | 0.3165 |
| Common dye support No. 2 | (*) | (*) |
| Demineralized water qs | 100 g | 100 g |

(**): comparative example not forming part of the invention
It is important to note that each of the dye compositions of Examples 5 and 6 above contains the same molar amount of additional coupler, i.e. $1.5 \times 10^{-3}$ mol.

| (***): Common dye support No. 2: | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 ® by the company Akzo | 7.0 g |
| Diethylaminopropyl laurylamino-succinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% $NH_3$ | 10.0 g |

At the time of use, each of the dye compositions described above was mixed with an equivalent amount by weight of 20-volumes hydrogen peroxide (6% by weight) having a pH of about 3.

Each resulting mixture had a pH of about 10±0.2, and was applied for 30 minutes to locks of permanent-waved grey hair containing 90% white hairs.

The hair was then rinsed with water, washed with a standard shampoo, rinsed again and then dried.

The colour of the locks was evaluated in the Munsell system using a Minolta CM 2002® spectrophotometer.

A test of resistance to permanent-waving was carried out on the locks of hair thus dyed.

To do this, the locks of hair were impregnated for 10 minutes with a reducing solution at a rate of 2 g of the reducing solution below per lock of 1 g:

Reducing solution:

| Thioglycolic acid | 6.7 g |
|---|---|
| Diammonium dithioglycolate at 48% in water | 5.0 g |
| Basifying agent qs | pH = 7.9 |
| Demineralized water qs | 100.0 g |

After rinsing, the locks of hair were immersed for 5 minutes in an oxidizing solution (consisting of an 8-volumes hydrogen peroxide solution of pH 3) at a rate of 2 g of oxidizing solution per lock of 1 g.

The locks were then rinsed with water and then dried for 1 hour at 60° C.

The colour of the locks of hair was then evaluated again in the Munsell system using a Minolta CM 2002® spectrophotometer.

The difference between the colour of the lock before permanent-waving and the colour of the lock after permanent-waving was calculated by applying the Nickerson formula:

$$\Delta E = 0.4 Co \Delta H + 6 \Delta V + 3 \Delta C$$

as described, for example, in "Couleur, Industrie et Technique [Colour, Industry and Technology]"; pages 14–17; Vol. No. 5; 1978.

In this formula, $\Delta E$ represents the difference in colour between two locks, $\Delta H$, $\Delta V$ and $\Delta C$ represent the variation in the absolute value of the parameters H, V and C, and Co represents the purity of the lock relative to which it is desired to evaluate the colour difference (before the test of resistance to permanent-waving).

The degradation of the colour ($\Delta E$) is proportionately greater the higher the value indicated.

The results are given in Table I below:

| EXAMPLE | Colour of the hair before permanent-waving | Colour of the hair after permanent-waving | Degradation of the colour | | | |
|---|---|---|---|---|---|---|
| | | | $\Delta H$ | $\Delta V$ | $\Delta C$ | $\Delta E$ |
| 5 | 0.8 P 1.8/1.6 | 3.9 P 2.0/3.5 | 3.1 | 0.2 | 1.9 | 8.9 |
| 6(**) | 1.1 P 1.8/1.7 | 6.2 P 2.3/4.5 | 5.1 | 0.5 | 2.8 | 14.9 |

(**)Example not forming part of the invention.

These results show that the dye composition of Example 5 in accordance with the invention, containing a combination of an oxidation base (para-phenylenediamine), 1,3-bis (β-hydroxyethyl)amino-2-methylbenzene as first coupler, and 2,4-diaminophenoxyethanol dihydrochloride as additional coupler in accordance with formula (I), gives a coloration which withstands the action of permanent-waving much better than the coloration obtained using the composition of Example 6, which does not form part of the invention since, instead of 2,4-diaminophenoxyethanol dihydrochloride, it contains 2,4-diamino-1-methoxybenzene dihydrochloride which does not form part of formula (I) and is as described, for example, in patent application FR 2,681,860.

What is claimed is:

1. A composition for the oxidation dyeing of keratin fibres comprising, in a medium which is suitable for dyeing:
   (a) at least one oxidation base,
   (b) and at least two couplers, wherein
      the first coupler is chosen from 1,3-bis(β-hydroxyethyl) amino-2-methylbenzene and an addition salt thereof with an acid, and
      the second coupler is chosen from a substituted meta-phenylenediamine corresponding to formula (I), and an addition salt thereof with an acid:

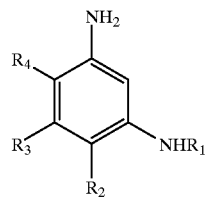

(I)

in which:
   $R_1$ is chosen from hydrogen, $C_1$–$C_4$ alkyl radicals, $C_1$–$C_4$ monohydroxyalkyl radicals and $C_2$–$C_4$ polyhydroxyalkyl radicals;,
   $R_2$ and $R_3$, which may be identical or different, are chosen from hydrogen, $C_1$–$C_4$ alkyl radicals and $C_1$–$C_4$ hydroxyalkoxy radicals; and
   $R_4$ is chosen from $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and 2,4-diaminophenoxyalkoxy radicals;
   provided that if $R_1$, $R_2$, and $R_3$ are simultaneously hydrogen, then $R_4$ is not a methoxy radical.

2. The composition according to claim 1, wherein the substituted meta-phenylenediamine of formula (I) is chosen from 2,4-diaminophenoxyethanol, 2,4-diamino-1-ethoxybenzene, 2-amino-4-N-(β-hydroxyethyl) aminoanisole, 3,5-diamino-1-ethyl-2-methoxybenzene, 3,5-diamino-2-methoxy-1-methylbenzene, 1,3-bis(2,4-diaminophenoxy)propane, bis-(2,4-diaminophenoxy) methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxy-propyloxy)benzene, 2-amino-4-N-(β-hydroxyethyl)amino-1-methoxybenzene, and an addition salt thereof with an acid.

3. The composition according to claim 1, wherein the oxidation base is chosen from a para-phenylenediamine, a double base, a para-aminophenol, an ortho-aminophenol, and a heterocyclic oxidation base.

4. The composition according to claim 3, wherein the para-phenylenediamine corresponds to formula (II), and an addition salt thereof with an acid:

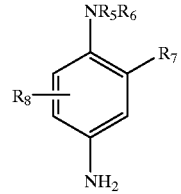

(II)

in which:
   $R_5$ is chosen from hydrogen, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, $C_1$–$C_4$ alkyl radicals substituted with a nitrogenous group, $C_1$–$C_4$ alkyl radicals substituted with a phenyl group, and $C_1$–$C_4$ alkyl radicals substituted with a 4'-aminophenyl group;
   $R_6$ is chosen from hydrogen, $C_1$–$C_4$ alkyl radicals, $C_1$–$C_4$ monohydroxyalkyl radicals, $C_2$–$C_4$ polyhydroxyalkyl radicals, $(C_1-C_4)$alkoxy$(C_1-C_4)$alkyl radicals, and $C_1-C_4$ alkyl radicals substituted with a nitrogenous group;

$R_7$ is chosen from hydrogen, halogen, $C_1-C_4$ alkyl radicals, $C_1-C_4$ monohydroxyalkyl radicals, $C_1-C_4$ hydroxyalkoxy radicals, $C_1-C_4$ acetylamino-alkoxy radicals, $C_1-C_4$ mesylaminoalkoxy radicals, and $C_1-C_4$ carbamoylaminoalkoxy radicals; and $R_8$ is chosen from hydrogen, halogen, and $C_1-C_4$ alkyl radicals.

5. The composition according to claim 4, wherein $R_7$ is a halogen chosen from chlorine, bromine, iodine, and fluorine.

6. The composition according to claim 4, wherein the para-phenylenediamine of formula (II) is chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-1 phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxy-ethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and an addition salt thereof with an acid.

7. The composition according to claim 3, wherein the double base corresponds to formula (III), and an addition salt thereof with an acid:

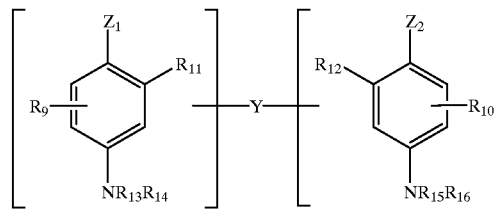

(III)

in which:

$Z_1$ and $Z_2$, which may be identical or different, are chosen from hydroxyl or —$NH_2$ radicals which can be substituted with $C_1-C_4$ alkyl radicals or with a linker arm Y; the linker arm Y is chosen from a linear or branched alkylene chain comprising from 1 to 14 carbon atoms, which can be interrupted or terminated with at least one nitrogenous group, with at least one hetero atom, or with a mixture thereof;

$R_9$ and $R_{10}$ are chosen from hydrogen, halogen atoms, $C_1-C_4$ alkyl radicals, $C_1-C_4$ monohydroxyalkyl radicals, $C_2-C_4$ polyhydroxyalkyl radicals, $C_1-C_4$ aminoalkyl radicals and a linker arm Y;

$R_{11}$, $R_{12}$, $R_{13}$, $R_{14}$, $R_{15}$ and $R_{16}$, which may be identical or different, are chosen from hydrogen, a linker arm Y and $C_1-C_4$ alkyl radicals;

provided that the compound of formula (III) comprises only one linker arm Y per molecule.

8. The composition according to claim 7, wherein the hetero atom that can interrupt or terminate the linker arm Y is chosen from oxygen, sulphur or nitrogen.

9. The composition according to claim 7, wherein the linker arm Y is substituted with at least one group chosen from a hydroxyl radical and $C_1-C_6$ alkoxy radicals.

10. The composition according to claim 7, wherein the double base of formula (III) is chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetra-methylenediamine, N,N'-bis (ethyl)-N,N'-bis(4'-amino-3'-methylphenyl) ethylenediamine, 1,8-bis(2,5-diaminophenoxy)-3,5-dioxaoctane, and an addition salt thereof with an acid.

11. The composition according to claim 3, wherein the para-aminophenol corresponds to formula (IV), and an addition salt thereof with an acid:

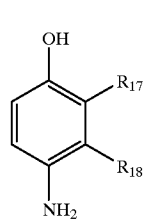

(IV)

in which:

$R_{17}$ is chosen from hydrogen, halogen atoms, $C_1-C_4$ alkyl radicals, $C_1-C_4$ monohydroxyalkyl radicals, $(C_1-C_4)$ alkoxy$(C_1-C_4)$alkyl radicals, $C_1-C_4$ aminoalkyl radicals and hydroxy$(C_1-C_4)$alkylamino$(C_1-C_4)$alkyl radicals; and $R_{18}$ is chosen from hydrogen, halogen atoms, $C_1-C_4$ alkyl radicals, $C_1-C_4$ monohydroxyalkyl radicals, $C_2-C_4$ polyhydroxyalkyl radicals, $C_1-C_4$ aminoalkyl radicals, cyano$(C_1-C_4)$alkyl radicals, and $(C_1-C_4)$alkoxy $(C_1-C_4)$alkyl radicals, provided that at least one of $R_{17}$ and $R_{18}$ is hydrogen.

12. The composition according to claim 11, wherein the para-aminophenol of formula (IV) is chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, and an addition salt thereof with an acid.

13. The composition according to claim 3, wherein the ortho-aminophenol is chosen from 2-aminophenol, 2-amino-5-methylphenol, 2-amino-6-methylphenol, 5-acetamido-2-aminophenol, and an addition salt thereof with an acid.

14. The composition according to claim 3, wherein the heterocyclic oxidation base is chosen from pyridine derivatives, pyrimidine derivatives, pyrazole derivatives, and an addition salt thereof with an acid.

15. The composition according to claim 1, wherein the oxidation base is present in said composition in an amount ranging from 0.0005 to 12% by weight relative to the total weight of the composition.

16. The composition according to claim 15, wherein the oxidation base is present in said composition in an amount ranging from 0.005 to 6% by weight relative to the total weight of the composition.

17. The composition according claim 1, wherein the first coupler is present in said composition in an amount ranging from 0.001 to 10% by weight relative to the total weight of the composition.

18. The composition according to claim 17, wherein the first coupler is present in said composition in an amount ranging from 0.01 to 5% by weight relative to the total weight of the composition.

19. The composition according to claim 1, wherein the second coupler is present in said composition in an amount ranging from 0.0001 to 10% by weight relative to the total weight of the composition.

20. The composition according to claim 17, wherein the second coupler is present in said composition in an amount ranging from 0.005 to 5% by weight relative to the total weight of the composition.

21. The composition according to claim 1, further comprising at least one additional coupler that is different from the first coupler and the second coupler, and at least one direct dye.

22. The composition according to claim 1, further comprising at least 1 one direct dye.

23. The composition according to claim 1, wherein the addition salt with an acid is chosen from a hydrochloride, a hydrobromide, a sulphate, a tartrate, a lactate, and an acetate.

24. The composition according to claim 1, wherein the keratin fibres are human keratin fibres.

25. The composition according to claim 24, wherein the human keratin fibres are hair.

26. A process for dyeing keratin fibres comprising the steps of 1) applying to said fibres at least one dye composition, and 2) developing a color at acidic, neutral or alkaline pH by adding an oxidizing agent to the dye composition at the time of applying to said fibres at least one dye composition, or wherein the oxidizing agent is present in an oxidizing composition that is applied simultaneously with the dye composition or sequentially after application of the dye composition, said at least one dye composition comprising, in a medium which is suitable for dyeing:

(a) at least one oxidation base,
(b) and at least two couplers, wherein
the first coupler is chosen from 1,3-bis(β-hydroxyethyl)amino-2-methylbenzene and an addition salt thereof with an acid, and
the second coupler is chosen from a substituted meta-phenylenediamine corresponding to formula (I), and an addition salt thereof with an acid:

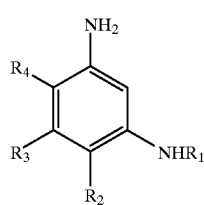

(I)

in which:
$R_1$ is chosen from hydrogen, $C_1$–$C_4$ alkyl radicals, $C_1$–$C_4$ monohydroxyalkyl radicals and $C_2$–$C_4$ polyhydroxyalkyl radicals;

$R_2$ and $R_3$, which may be identical or different, are chosen from hydrogen, $C_1$–$C_4$ alkyl radicals and $C_1$–$C_4$ hydroxyalkoxy radicals; and $R_4$ is chosen from $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and 2,4-diaminophenoxyalkoxy radicals;

provided that if $R_1$, $R_2$ and $R_3$ are simultaneously hydrogen, then $R_4$ is not a methoxy radical.

27. The process according to claim 26, wherein the oxidizing agent present in the oxidizing composition is chosen from hydrogen peroxide, urea peroxide, an alkali metal bromate, a persalt, a peracid, and an enzyme.

28. The process according to claim 27, wherein the persalt is chosen from perborates, percarbonates, and persulphates.

29. The process according to claim 26, wherein the keratin fibers are human keratin fibres.

30. The process according to claim 29, wherein the human keratin fibers are hair.

31. A multi-compartment dyeing kit comprising a first compartment that contains a dye composition for the oxidation dyeing of keratin fibers comprising, in a medium which is suitable for dyeing:

(a) at least one oxidation base,
(b) and at least two couplers, wherein
the first coupler is chosen from 1,3-bis(β-hydroxyethyl)amino-2-methylbenzene and an addition salt thereof with an acid, and
the second coupler is chosen from a substituted meta-phenylenediamine corresponding to formula (I), and an addition salt thereof with an acid:

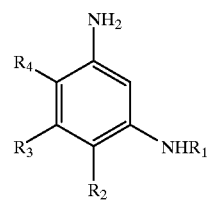

(I)

in which:
$R_1$ is chosen from hydrogen, $C_1$–$C_4$ alkyl radicals, $C_1$–$C_4$ monohydroxyalkyl radicals and $C_2$–$C_4$ polyhydroxyalkyl radicals;

$R_2$ and $R_3$, which may be identical or different, are chosen from hydrogen, $C_1$–$C_4$ alkyl radicals and $C_1$–$C_4$ hydroxyalkoxy radicals; and $R_4$ is chosen from $C_1$–$C_4$ alkoxy radicals, $C_1$–$C_4$ aminoalkoxy radicals, $C_1$–$C_4$ monohydroxyalkoxy radicals, $C_2$–$C_4$ polyhydroxyalkoxy radicals and 2,4-diaminophenoxyalkoxy radicals;

provided that if $R_1$, $R_2$, and $R_3$ are simultaneously hydrogen, then $R_4$ is not a methoxy radical; and a second compartment that contains an oxidizing composition.

* * * * *

UNITED STATES PATENT AND TRADEMARK OFFICE
CERTIFICATE OF CORRECTION

PATENT NO. : 6,391,063 B1 Page 1 of 1
DATED : May 21, 2002
INVENTOR(S) : Marie-Pascale Audousset It is certified that error appears in the above-identified patent and that said Letters Patent is hereby corrected as shown below:

Column 12,
Line 13, insert space between "C1-C4" and -- alkyl --.

Column 13,
Line 16, "2,6-diethyl-para-1-phenylenediamine" should read
-- 2,6-diethyl-para-phenylenediamine --

Signed and Sealed this

Thirtieth Day of July, 2002

Attest:

JAMES E. ROGAN
Attesting Officer                   Director of the United States Patent and Trademark Office